(12) United States Patent
Tinge et al.

(10) Patent No.: US 9,908,785 B2
(45) Date of Patent: Mar. 6, 2018

(54) PROCESS AND APPARATUS FOR PRODUCING AMMONIUM SULFATE CRYSTALS

(71) Applicant: CAP III B.V., Sittard (NL)

(72) Inventors: Johan Thomas Tinge, Sittard (NL); Geert Ekkelenkamp, Echt (NL); Robert Geertman, Echt (NL)

(73) Assignee: CAP III B.V., Sittard (NL)

( * ) Notice: Subject to any disclaimer, the term of this patent is extended or adjusted under 35 U.S.C. 154(b) by 12 days.

(21) Appl. No.: 14/899,579

(22) PCT Filed: Jun. 20, 2014

(86) PCT No.: PCT/EP2014/062987
§ 371 (c)(1),
(2) Date: Dec. 18, 2015

(87) PCT Pub. No.: WO2014/206869
PCT Pub. Date: Dec. 31, 2014

(65) Prior Publication Data
US 2016/0159657 A1    Jun. 9, 2016

(30) Foreign Application Priority Data

Jun. 24, 2013 (EP) .................................... 13173325

(51) Int. Cl.
| | |
|---|---|
| *B01D 9/00* | (2006.01) |
| *C01C 1/24* | (2006.01) |
| *C01C 1/248* | (2006.01) |
| *C07D 201/16* | (2006.01) |
| *C07D 201/04* | (2006.01) |
| *C07C 249/08* | (2006.01) |

(52) U.S. Cl.
CPC ............... *C01C 1/24* (2013.01); *B01D 9/004* (2013.01); *B01D 9/0022* (2013.01); *B01D 9/0031* (2013.01); *B01D 9/0063* (2013.01); *C01C 1/248* (2013.01); *C07C 249/08* (2013.01); *C07D 201/04* (2013.01); *C07D 201/16* (2013.01); *B01D 2009/0086* (2013.01); *C07C 2601/14* (2017.05)

(58) Field of Classification Search
CPC ....... B01D 9/00; B01D 9/0022; C01B 11/185; C01C 1/24
USPC ...................................................... 23/302 A
See application file for complete search history.

(56) References Cited

U.S. PATENT DOCUMENTS

| 3,530,924 A | 9/1970 | Domning |
| 2011/0038781 A1 | 2/2011 | Hoffman |

FOREIGN PATENT DOCUMENTS

| GB | 748572 | 5/1956 |
| JP | 2010-163319 | 7/2010 |

OTHER PUBLICATIONS

International Search Report for PCT/EP2014/062987 dated Oct. 21, 2014.
Kawakami, Tadao, "Industrial application of nonaqueous solution chemistry", Chemical Engineering, vol. 23, No. 2, 1959, p. 45.

*Primary Examiner* — Edward Johnson
(74) *Attorney, Agent, or Firm* — Honigman Miller Schwartz and Cohn LLP; Andrew N. Weber; Jonathan P. O'Brien (57) ABSTRACT

The present invention provides a continuous process for producing ammonium sulfate crystals, wherein said process comprises:
(a) feeding to a first group of crystallization sections, which crystallization sections are heat integrated in series, a first aqueous ammonium sulfate solution that contains one or more impurities;
(b) feeding to a second group of crystallization sections, which crystallization sections are heat integrated in series, a second aqueous ammonium sulfate solution that contains one or more impurities;
(c) crystallizing ammonium sulfate crystals in each crystallization section respectively from each of said solutions of ammonium sulfate that contain one or more impurities;
(d) purging a fraction of the ammonium sulfate solution that contains one or more impurities from each of said crystallization sections; and
(e) discharging ammonium sulfate crystals from each crystallization section, characterized in that:
  (i) both the first group of crystallization sections and the second group of crystallization sections are together heat integrated in one series of crystallization sections; wherein the first group of crystallization sections operates at higher temperature than the second group of crystallization sections; and
  (ii) the composition of the first aqueous ammonium sulfate solution that contains one or more impurities is different to the composition of the second aqueous ammonium sulfate solution that contains one or more impurities.

Further provided is apparatus suitable for producing ammonium sulfate crystals.

10 Claims, 3 Drawing Sheets

PROCESS AND APPARATUS FOR PRODUCING AMMONIUM SULFATE CRYSTALS

This U.S. nonprovisional application is the 35 USC §371 national phase of PCT Application No. PCT/EP2014/062987, filed on Jun. 20, 2014, which claims the benefit of EP Application No. 13173325.5, filed on Jun. 24, 2013. Each of these documents is hereby incorporated by reference in its entirety.

The invention relates to a process for preparing ammonium sulfate crystals.

Ammonium sulfate ($(NH_4)_2SO_4$) is a product which is produced on a large scale. This inorganic salt has a number of commercial uses, but is used mainly as fertilizer in agriculture to provide nitrogen and sulfur. It contains 21% nitrogen as ammonium cations, and 24% sulfur as sulfate anions. Ammonium sulfate crystals for this use are classified according to crystal size.

In almost all commercial caprolactam production processes ammonium sulfate is obtained as by-product. The ammonium sulfate might be produced during the formation of the intermediate cyclohexanone oxime and/or during the Beckmann rearrangement of cyclohexanone oxime into caprolactam.

Hydroxylamine sulfate may be produced by the so-called Raschig processes (including conventional Raschig process and Direct Raschig process), using ammonium salts as starting materials. Oximation of cyclohexanone is then carried out with aqueous hydroxylammonium sulfate solution. In general ammonia is added to liberate the hydroxylammonium, whereby ammonium sulfate is formed. The amount of ammonium sulfate formed during oximation is typically about 2.7 tons per ton of cyclohexanone oxime.

Hydroxylammonium sulfate solution may alternatively be obtained by hydrogenation of nitric oxide over a platinum catalyst in the presence of dilute sulfuric acid. The hydroxylammonium sulfate solution is reacted with cyclohexanone and ammonia to form cyclohexanone oxime and ammonium sulfate. This process for the production of hydroxylammonium sulfate solution typically generates about 0.8 tons of ammonium sulfate per ton of cyclohexanone oxime during the oximation step.

In the Beckmann rearrangement reaction of cyclohexanone oxime, either sulfuric acid or oleum or $SO_3$ is used as rearrangement medium. The reaction gives the sulfate of caprolactam in excess sulfuric acid, which is then neutralized with ammonia or ammonia water. This process for the production of caprolactam from cyclohexanone oxime typically generates in the range of from 1.4 to 1.8 tons of ammonium sulfate per ton of converted cyclohexanone oxime.

Most industrial acrylonitrile is produced by catalytic ammoximation of propene. Ammonia is separated from the product stream using sulfuric acid, resulting in an ammonium sulfate solution. This process for the production of acrylonitrile from propene typically generates about 0.2 tons of ammonium sulfate per ton of produced acrylonitrile.

Ammonium sulfate crystals may be obtained by subjecting an ammonium sulfate solution to crystallization and subjecting the resulting slurry of ammonium sulfate crystals to a size classification step.

In general, ammonium sulfate crystals are obtained, in a crystallization step, from the ammonium sulfate solution by evaporating the solvent, which solvent usually is water. Examples of crystallizers are described in "Perry's Chemical Engineers Handbook" by Don W. Green and James O. Maloney, 7th edition, McGraw Hill, 1997, Section 18, pages 44-55. The temperature and pressure at which the crystallizer is operated are not critical. However, the crystallizer usually is operated at a temperature of between 20 and 180° C. and at a pressure of between 2 kPa and 0.8 MPa.

Crystallization by evaporation typically involves heat input to evaporate solvent and concentrate the remaining solution. In order to reduce steam consumption needed for evaporative crystallization in the production of sodium chloride crystals from aqueous sodium chloride solutions, for example, a series of crystallizers are in general integrated with respect to heat input (see e.g. I. Kristjansson, Geothermics, 21 (1992); pp 765-771). In a series of heat integrated crystallization sections, water is boiled in a sequence of crystallizers, each held at a lower pressure than the last. Because the boiling temperature of water decreases as pressure decreases, the vapor boiled off in one crystallizer can be used to heat the next, and only the first crystallizer (at the highest pressure) requires an external source of heat. This is commonly done by passing steam at a high temperature into the reboiler of the first crystallizer in a series. The resulting lower temperature steam is used to heat the next crystallizer, and so on. This means that a series of crystallizers operates at descending temperatures. The size and conditions of the crystallizers are optimized for this heating arrangement.

Unlike single-stage evaporative crystallizers, a series of heat integrated crystallization sections can be made of up to seven evaporator stages or effects. The energy consumption for a single-effect evaporative crystallizer is very high and makes up most of the variable cost for an evaporation system. Putting together evaporators saves heat and thus requires less energy. Adding one evaporator to the original decreases the energy consumption to 50% of the original amount. Adding another effect reduces it to 33% and so on. In practice the realized savings are somewhat less, amongst other due to energy required for preheating of the feeds to boiling temperatures.

US2011/0038781A1 describes a process and apparatus for the crystallization of ammonium sulfate, comprising a precrystallizer which provides heating from vapour of reaction in series to three crystallizers. The crystallizers are operated in parallel with respect to ammonium sulfate production from a single source.

Impurities present in aqueous ammonium sulfate solutions obtained as by-product during the production of, for example, cyclohexanone oxime, caprolactam or acrylonitrile, tend to form visible solid impurities under the conditions of evaporative crystallization. The presence of such visible solid impurities has a negative impact on the quality of the produced ammonium sulfate crystals. Formation of visible solid impurities is more pronounced during crystallization at higher temperatures. Accordingly, it is desirable not to crystallize the ammonium sulfate solution at higher temperatures. Because heating of a series of crystallizers is by multiple effect, avoiding crystallizers that are operated at high temperatures limits the number of crystallizers possible in the series. Therefore optimum use of available heat is not made. Heat consumption of a series of crystallizers is accordingly higher than otherwise possible.

During conventional operation of an evaporative crystallizer, impurities become concentrated in the solution. Accordingly, a purge is employed, whereby solution is, continuously or periodically, discharged from the crystallizer. In a conventional series of crystallization sections, each crystallization section operates at the same concentration of impurity. The purge therefore reduces the amount of visible solid impurities in the ammonium sulfate crystals. However, the purge does not adequately prevent formation of visible solid impurities. Further, purging also removes ammonium sulfate solution from the crystallization section, thereby reducing the yield of ammonium sulfate crystals from solution. This has a negative impact on the economics of ammonium sulfate crystal production.

The present inventors have recognised that the formation of visible solid impurities is dependent on the impurities in the ammonium sulfate solution. The temperature at which a given ammonium sulfate solution may be crystallized without formation of visible solid impurities is dependent on both the quantity and the composition of its impurities. Accordingly, where two or more sources of ammonium sulfate having different compositions of impurity are to be crystallized, different upper temperatures may be used for each source. Rather than combining such sources and crystallizing them commonly, separate crystallizations at different temperatures may be used for each source. Further it was found that the crystallizations could be carried out separately, but integrated with respect to heat supply in one series of crystallization sections.

Accordingly, the present invention provides a continuous process for producing ammonium sulfate crystals, wherein said process comprises:

(a) feeding to a first group of crystallization sections, which crystallization sections are heat integrated in series, a first aqueous ammonium sulfate solution that contains one or more impurities;

(b) feeding to a second group of crystallization sections, which crystallization sections are heat integrated in series, a second aqueous ammonium sulfate solution that contains one or more impurities;

(c) crystallizing ammonium sulfate crystals in each crystallization section respectively from each of said solutions of ammonium sulfate that contain one or more impurities;

(d) purging a fraction of the ammonium sulfate solution that contains one or more impurities from each of said crystallization sections; and (e) discharging ammonium sulfate crystals from each crystallization section, characterized in that:

(i) both the first group of crystallization sections and the second group of crystallization sections are together heat integrated in one series of crystallization sections; wherein the first group of crystallization sections operates at higher temperature than the second group of crystallization sections; and (ii) the composition of the first aqueous ammonium sulfate solution that contains one or more impurities is different to the composition of the second aqueous ammonium sulfate solution that contains one or more impurities.

The present invention further provides apparatus suitable for producing ammonium sulfate crystals, said apparatus comprising:

(i) a first series of crystallization sections, comprising:

(a) a plurality of crystallization sections, each crystallization section comprising a purge outlet;

(b) a first material feed system connected to each crystallization section in the first series;

(c) a first product removal system connected to each crystallization section in the first series;

(d) a first steam supply system integrating the crystallization sections in series;

(ii) a second series of crystallization sections, comprising:

(a) a plurality of crystallization sections, each crystallization section comprising a purge outlet;

(b) a second material feed system connected to each crystallization section in the second series;

(c) a second product removal system connected to each crystallization section in the second series;

(d) a second steam supply system integrating the crystallization sections in series;

characterized in that the first steam supply system is connected to the second steam supply system and the first material feed system is not connected to the second material feed system.

As used herein, a crystallization section comprises all equipment necessary to accept an ammonium sulfate solution, and discharge ammonium sulfate crystals. In its simplest form this means a crystallizer and a separation unit.

A group of crystallization sections, which crystallization sections are heat integrated in series means that heat is applied to the crystallization section at one end of the group; heat is then transferred, directly or indirectly, to the next crystallization section in the group; and so on until the last crystallization section in the group. In this way, a single external heat source is used to heat all crystallization sections in the group, but is applied directly only to the first.

By purging a fraction of the ammonium sulfate solution is meant that a fraction of the ammonium sulfate solution is discharged from the crystallization section. The purpose of the purge is to reduce the impurity content in the ammonium sulfate solution, thereby also reducing the impurity content of the crystallized ammonium sulfate.

An ammonium sulfate solution consists just of solvent, impurities and (pure) ammonium sulfate. The composition of the first aqueous ammonium sulfate solution is different to the composition of the second aqueous ammonium sulfate solution in at least one of concentration of ammonium sulfate and concentration and nature of impurities. Impurities may be organic or inorganic impurities or both. The compositions of the impurities are typically different in the first and second feed.

Ammonium sulfate crystals consist, besides some remaining solvent, just of impurities and (pure) ammonium sulfate.

Together heat integrated in one series means that the two groups of crystallization sections form one series. A series of crystallization sections, which crystallization sections are heat integrated in series means that heat is applied to the crystallization section at one end of the series; heat is then transferred, directly or indirectly, to the next crystallization section in the series; and so on until the last crystallization section in the series. In this way, a single external heat source is used to heat all crystallization sections in the series, but is applied directly only to the first. The solutions of ammonium sulfate that contain one or more impurities fed to each group of crystallization sections may be mixed, but preferably remain independent. Accordingly, there is preferably no purge from one group of crystallization sections to another group of crystallization sections. Optionally, a purge from a crystallization section might be fed to another crystallization section.

The first group of crystallization sections operates at a higher temperature than the second group of crystallization sections. Therefore the first group is positioned earlier in the heat integration series than the second group.

The apparatus of the present invention comprises crystallization sections which are configured to be heat integrated with respect to steam. By this it is meant that steam is the heat source, and that the series of crystallization sections comprises the necessary pipework that heat can be transferred by input of steam to the first crystallization section in the series, and the heat transferred throughout the series, as described above. The temperature of successive crystallization sections in the series is therefore successively lower. Therefore, there is a direction of descending temperature of steam supply, from the first crystallization section to the last crystallization section in the series.

Crystals of a larger size are preferred, because they generally have a larger economic value. Typically, the mean median diameter of crystals produced is greater than 0.8 mm. Preferably, the mean median diameter of the ammonium sulfate crystals discharged is from 1.0 mm to 4.0 mm.

The formation of visible solid impurities is reduced by employing the method and apparatus of the present invention. Visible solid impurities comprise dark coloured solid impurities. These are, in particular solid impurities with a high, and even majority, organic content. Typical impurities arise from the method by which the ammonium sulfate solution is produced. The nature of impurities is typically different in the two different feeds of aqueous ammonium sulfate solution.

Preferably, the ammonium sulfate solution is produced from a process for producing ε-caprolactam or acrylonitrile. Accordingly, the impurities present are typically those commonly produced in such reactions and/or already available in its raw materials. A blend of impurities from different sources could require typically high mother liquor purging rates. For example, the blend of nitrate impurity, typical from cyclohexanone oxime synthesis of hydroxylamine sulfate; together with impurities having high chemical oxygen demand (COD), typical from the Beckmann rearrangement of cyclohexanone oxime is, especially after removing of solvent, potentially explosive. Processing two aqueous ammonium sulfate feeds independently avoids such a blend being formed.

In addition this method allows a reduced overall purge of ammonium sulfate comprising mother liquor resulting in the production of an increased fraction of pure ammonium sulfate crystals.

Heat integration may be achieved by any suitable means. For example, by vapour recompression or by multiple effect evaporation (also called evaporation in effect). Preferably the crystallization sections are heat integrated by means of multiple effect evaporation. Various heat sources can be used as energy source for the evaporation of solvent in the first evaporator of a series of evaporators. Preferably steam is used as heat source for the evaporation of solvent in the first evaporator of a series of evaporators. Accordingly, preferably the crystallization sections are heat integrated by means of steam. Steam is readily available as a heat source on chemical production facilities.

A particular advantage of the present invention is that two or more sources of ammonium sulfate having different impurity profiles may be used. This allows efficient processing of ammonium sulfate produced as by-product from two or more different processes. Typically the first aqueous ammonium sulfate solution that contains one or more impurities and the second aqueous ammonium sulfate solution that contains one or more impurities are each produced as a by-product during the production of another chemical product. Preferably, the first aqueous ammonium sulfate solution that contains one or more impurities and the second aqueous ammonium sulfate solution that contains one or more impurities are each produced as a by-product during the production of cyclohexanone oxime, caprolactam and/or acrylonitrile.

Typically the first aqueous ammonium sulfate solution that contains one or more impurities is produced as a by-product during the production of cyclohexanone oxime. Preferably, it is obtained as a by-product during the production of cyclohexanone oxime via oximation of cyclohexanone with aqueous hydroxylammonium sulfate.

Typically the second aqueous ammonium sulfate solution that contains one or more impurities is produced as a by-product during the production of caprolactam. Preferably, it is produced as a by-product during the production of caprolactam obtained by Beckmann rearrangement of cyclohexanone oxime in oleum, sulfuric acid, or $SO_3$.

Typically the first aqueous ammonium sulfate solution that also contains one or more impurities and the second aqueous ammonium sulfate solution that also contains one or more impurities are each produced as by-products during the production of cyclohexanone oxime obtained via oximation of cyclohexanone with aqueous hydroxylammonium sulfate, caprolactam obtained by Beckmann rearrangement of cyclohexanone oxime in oleum, sulfuric acid, or $SO_3$ and/or acrylonitrile obtained by ammoximation of propene.

In principle, any number of crystallization sections may be used in a group of crystallization sections. However, typically, a group of crystallization sections comprises from 1 to 4 crystallization sections. Preferably, it comprises 2 or 3 crystallization sections. A series of crystallization sections typically comprises from 2 to 8 crystallization sections. Preferably, the series of crystallization sections comprises from 2 to 5 crystallization sections.

Typically the temperature of steam entering the first crystallization section in the series of crystallization sections is from 80° C. to 160° C. Preferably, it is from 100° C. to 140° C., for example 120° C.

Typically the temperature of steam exiting the last crystallization section in the series of crystallization sections is from 40° C. to 90° C. Preferably, it is from 45° C. to 75° C., more preferably, it is from 45° C. to 55° C., for example 50° C.

Typically, the ammonium sulfate is crystallized from the aqueous phase under acid conditions. Preferably ammonium sulfate is crystallized from the aqueous phase at a pH of from 2 to 6; more preferably from 4 to 5 (as determined at a temperature of 25° C.).

Typically, each crystallization section in the series of crystallization sections has substantially equal production capacity of ammonium sulfate crystals. As used herein, the term substantially equal production capacity of ammonium sulfate crystals means that production capacity typically deviates by less than 10% between crystallization sections. Preferably, it is less than 5%; more preferably less than 2%. Production capacity is typically measured as mass of product produced in unit time. For example, in kg per hour, or kilotons per annum (kta).

Typically a fraction of aqueous ammonium sulfate solution that also contains one or more impurities is purged from at least one crystallization section in a group to at least one other crystallization section in the same group.

The purity of the majority of crystals produced by a group of crystallization sections may be increased. By purging from one crystallization section in the group to another crystallization section in the group, the mean concentration of impurities in the group of crystallization sections can be reduced. Further, the system of purging can be arranged such that the purity of product crystals from all but one of the crystallization sections in the group is far higher than that of the prior art. Accordingly, the produced crystals can be further processed as a particularly pure product and a less pure product. Or the products can be combined to produce a product which is on average more pure than a system without purge coupling.

Typically the crystallization sections are heat integrated by means of steam, and a fraction of aqueous ammonium sulfate solution that also contains one or more impurities is purged from each crystallization section in a group to the next crystallization section, as defined by descending temperature of steam supply, in the same group, with the exception that the purge from the final crystallization section in the group is discharged from the group. In such a way impurity build-up to levels that are undesired in each of the crystallization sections is avoided.

Typically, each crystallization section comprises an evaporative crystallizer and solid-liquid separation equipment. The crystallizer may be of any suitable type. However, preferably, each crystallization section comprises an Oslo-type crystallizer. Oslo-type crystallizers are particularly suitable for the present invention because they are capable of producing crystals of larger mean median diameter. That is in general desirable for ammonium sulfate crystals.

Solid-liquid separation equipment means any equipment suitable to separate ammonium sulfate crystals from a solution comprising ammonium sulfate. It may include a continuous filter, a centrifuge, a decanter, an elutriation column, a hydrocyclone, a salt leg or a combination thereof. For example, it may comprise a salt leg in combination with an elutriation column and a centrifuge. Typically, before leaving the crystallization section the ammonium sulfate crystals are washed with water or an aqueous ammonium sulfate solution. Typically, after leaving the crystallization section the resulting ammonium sulfate crystals are discharged to a drying section. Crystals from each crystallization section may be combined either before or after drying.

In the apparatus of the present invention, the steam supply system includes an heat integration of the first steam supply system and the second steam supply system. In this way the steam supply system may be a single system heat integrating both the first series of crystallization sections and the second series of crystallization sections in series. The material feed system may feed a solution or a slurry. Preferably it is for a solution of ammonium sulphate or a slurry of ammonium sulphate. Preferably, the first product removal system is connected to the second product removal system.

In a preferred embodiment, the apparatus of the present invention is suitable for producing ammonium sulfate crystals, said apparatus comprising:

(a) a series of crystallization sections, which are configured to be heat integrated with respect to steam;

(b) a steam supply system integrating the crystallization sections in series;

(c) a feed system configured to provide aqueous ammonium sulfate solution that contains one or more impurities to the series of crystallization sections;

(d) a purge system from each crystallization section; and (e) a system of removal of ammonium sulfate crystals from each crystallization section;

characterized in that, (i) the series of crystallization sections comprises a first group of crystallization sections, and a second group of crystallization sections wherein the first group of crystallization sections is configured to receive steam of a higher temperature than the steam supplied to the second group of crystallization sections; and (ii) the feed system comprises a first feed configured to provide a first aqueous ammonium sulfate solution that contains one or more impurities to the first group of crystallization sections; and a second feed configured to provide a second aqueous ammonium sulfate solution that contains one or more impurities to the second group of crystallization sections.

The apparatus of the present invention is typically an ammonium sulfate crystallization plant. Typically, such a plant is integrated with one or more other chemical plants. For example a plant for the production of caprolactam and/or cyclohexanone oxime and/or acrylonitrile. Capacity of the ammonium sulfate crystallization plant is typically selected based on the volume of ammonium sulfate solution discharged from the other chemical plants. Further, crystallization section size is selected based on optimum conditions. Typically, the production capacity of ammonium sulfate crystals of each crystallization section is on the scale of thousands of tons per year (kilotons per annum; kta). Typically the production capacity of ammonium sulfate crystals of each crystallization section is more than 10,000 tons per annum (10 kta). Preferably, it is from 10 kta to 200 kta. More preferably, the production capacity of each crystallization section is from 30 kta to 150 kta.

For a series of crystallization sections, it is preferred that the crystallization sections are each of the same size and type, because of lower investment costs. The production capacity is important, because the steam used from one effect is used for the next effect, as described in Kristjansson in Geothermics 21 (1992) 765-771. A further advantage of having substantially equal production capacity is that equipment can be standardized. The crystallizer and the separation units, for example centrifuges and filters, are preferably respectively each of the same type. Typically each of the crystallization sections in the series has substantially equal production capacity to the other crystallization sections in the series. In other words each of the crystallizers in the first series has substantially equal production capacity to the other crystallizers in the first series, and each of the crystallizers in the second series has substantially equal production capacity to the other crystallizers in the second series.

The present invention will be more fully explained with reference to the following drawings.

Figure 1:
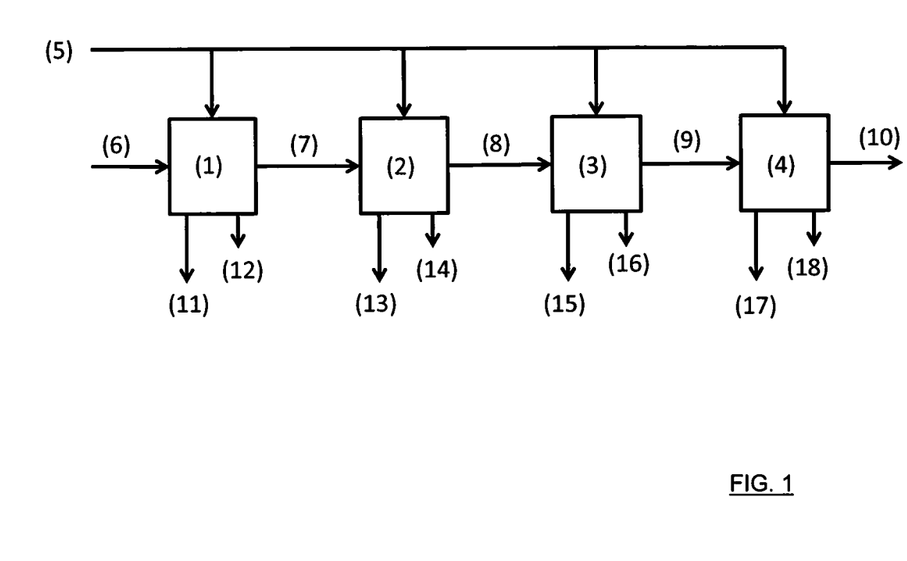
FIG. 1 describes an embodiment of the prior art, wherein four crystallization sections are arranged in parallel in view of the feed of ammonium sulfate solution.

FIG. 1 describes an embodiment of the prior art. Four crystallization sections, (1), (2), (3), (4), each comprising a crystallizer of equal size are arranged in parallel with respect to the feed of ammonium sulfate solution. An ammonium sulfate solution passes through feed line (5) into each crystallization section, where crystallization occurs to form a slurry of ammonium sulfate crystals in an ammonium sulfate solution. The ammonium sulfate solution that passes through feed line (5) might originate from one single source or might have been obtained by blending two or more solutions of ammonium sulfate originating from different sources.

Steam is fed to the crystallization section (1), via line (6), where it is used to evaporate solvent from the ammonium sulfate solution, thereby aiding crystallization. The steam does not directly contact the ammonium sulfate solution, but transfers heat indirectly thereto via a heat exchange unit. A solvent-comprising vapor stream is formed in crystallization section (1), and is discharged through line (7) to crystallization section (2), where it is used to evaporate solvent, analogous to the process in crystallization section (1). The solvent-comprising vapor stream formed in crystallization section (2) is discharged through line (8) to crystallization section (3) where it is used to evaporate solvent analogous to the process in crystallization section (1). The solvent-comprising vapor stream formed in crystallization section (3) is discharged through line (9) to crystallization section (4) where it is used to evaporate solvent analogous to the process in crystallization section (1). The solvent-comprising vapor stream formed in crystallization section (4) is discharged via line (10). Ammonium sulfate crystals are discharged from crystallization section (1) though line (11) for further processing. A fraction of ammonium sulfate solution comprising impurities is purged through line (12). Ammonium sulfate crystals are discharged from crystallization section (2) though line (13) for further processing. A fraction of ammonium sulfate solution comprising impurities is purged through line (14). Ammonium sulfate crystals are discharged from crystallization section (3) though line (15) for further processing. A fraction of ammonium sulfate solution comprising impurities is purged through line (16). Ammonium sulfate crystals are discharged from crystallization section (4) though line (17) for further processing. A fraction of ammonium sulfate solution comprising impurities is purged through line (18). Optionally, the ammonium sulfate crystals from lines (11), (13), (15) and (17) are combined, either before or after any further processing step. The solutions of ammonium sulfate purged through lines (12), (14), (16) and (18) are treated as waste, and undergo further processing. Optionally, these purged solutions of ammonium sulfate are fed to another crystallization section. Optionally, these solutions of ammonium sulfate are combined.

Figure 2:
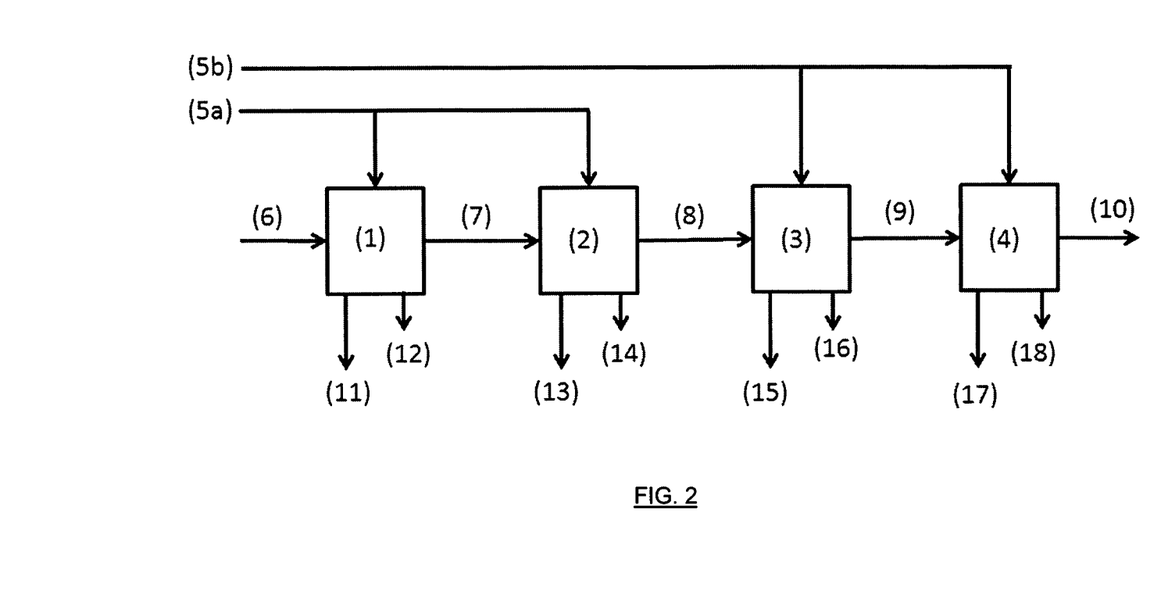
FIG. 2 describes an embodiment of the present invention, wherein the common feed line is adapted to enable feeding solutions of ammonium sulfate with different compositions to two groups of two crystallization sections.

FIG. 2 describes an embodiment of the present invention. The system is essentially the same as that of FIG. 1. Specifically, crystallization sections (1), (2), (3) and (4); the steam system (6), (7), (8), (9), (10); the four lines through which ammonium sulfate crystals are discharged from the crystallization sections (11), (13), (15), (17); and purge lines (12), (14), (16) and (18) are identical to those of FIG. 1.

The feeds of solutions of ammonium sulfate to crystallization sections (1), (2), (3) and (4) are adapted. Instead of feeding a common aqueous ammonium sulfate solution to each of the crystallization sections (1), (2), (3) and (4), a first aqueous ammonium sulfate solution that contains one or more impurities is fed via line (5a) to a first group of crystallization sections, comprising (1) and (2); and a second aqueous ammonium sulfate solution that contains one or more impurities is fed via line (5b) to a second group of crystallization sections, comprising (3) and (4).

Figure 3:
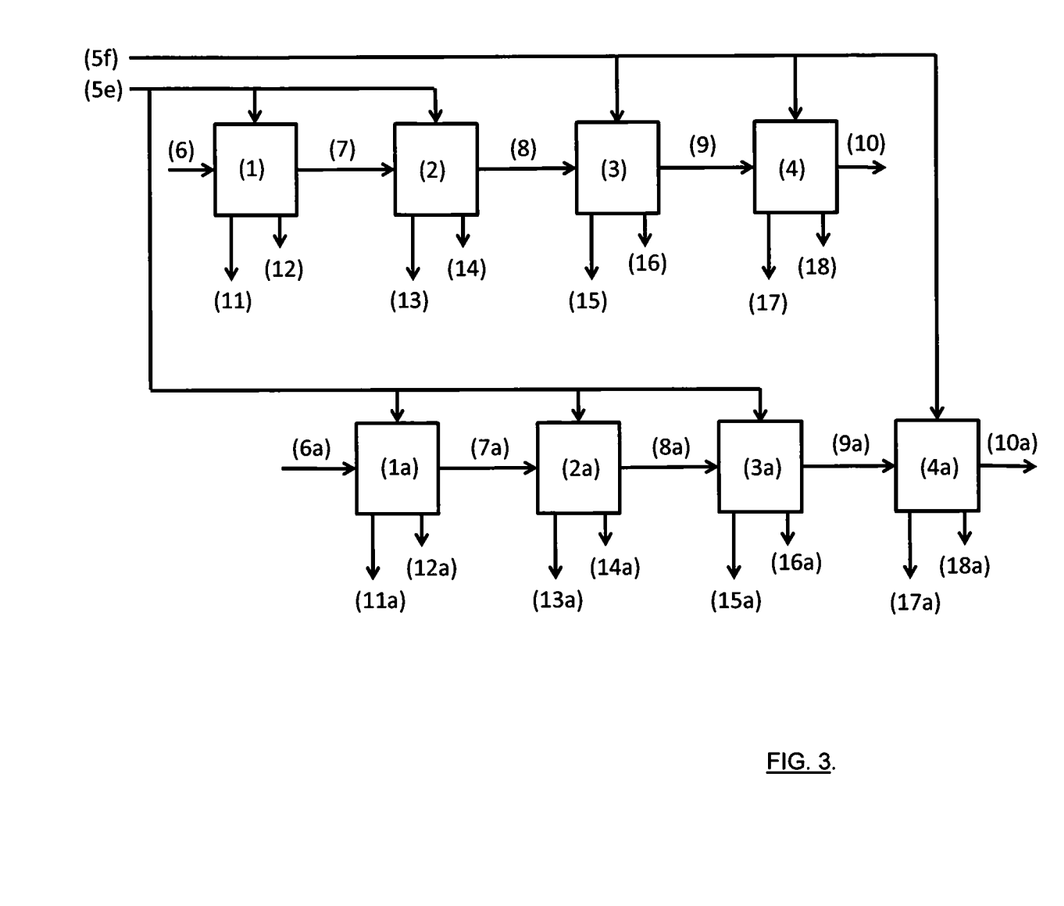
FIG. 3 describes an embodiment of the present invention comprising two parallel series, each of four crystallization sections, each series heat integrated in effect. Two feed ammonium sulfate solutions are fed to four groups of crystallization sections across the two series.

FIG. 3 describes an embodiment of the present invention. The system is similar to that of FIG. 2 except that it comprises two parallel series of four crystallizers, each series being heat integrated. Specifically, crystallization sections (1), (2), (3) and (4); the steam system (6), (7), (8), (9), (10); the four lines through which ammonium sulfate crystals are discharged from these crystallization sections (11), (13), (15), (17); and purge lines (12), (14), (16) and (18) are identical to those of FIG. 2. A parallel series of crystallization sections, (1a), (2a), (3a) and (4a); steam system (6a), (7a), (8a), (9a), (10a); lines through which ammonium sulfate crystals are discharged from these crystallization sections (11a), (13a), (15a), (17a); and purge lines (12a), (14a), (16a) and (18a) are analogous to the first series of crystallization sections described with reference to FIG. 2. These correspond to the numbered components of FIG. 2 without the 'a'.

The feeds of aqueous ammonium sulfate solutions to the crystallization sections are adapted. To crystallization sections (1), (2), (1a), (2a) and (3a) a first aqueous ammonium sulfate solution is fed via line (5e). To crystallization sections (3), (4) and (4a) a second aqueous ammonium sulfate solution is fed via line (5f). To each crystallization section roughly a similar amount of ammonium sulfate solution is fed. Accordingly, crystallization sections (1) and (2) form a first group; crystallization sections (3) and (4) form a second group; crystallization sections (1a), (2a) and (3a) form a third group; and crystallization section (4a) forms a fourth group.

The invention is illustrated by but not intended to be limited to the following Examples.

EXAMPLE 1

In a commercial caprolactam plant cyclohexanone oxime was produced according to the Raschig route from cyclohexanone produced via hydrogenation of phenol. The cyclohexanone oxime was converted into caprolactam in a multi-stage Beckmann rearrangement process with oleum. The obtained caprolactam was recovered after neutralization with aqueous ammonia. In each of the cyclohexanone oxime formation step and caprolactam formation step, aqueous ammonia was used for neutralization. As a result an aqueous ammonium sulfate solution was obtained as by-product in each step.

The composition of the aqueous ammonium sulfate solution obtained in the cyclohexanone oxime formation step was:

| | |
|---|---|
| Ammonium sulfate | ca. 43.5 wt. % |
| Water | ca. 54.4 wt. % |
| Free $H_2SO_4$ | <0.1 wt. % |
| COD | ca. 120 ppm |
| Ammonium nitrate | ca. 2.1 wt. % |

The composition of the aqueous ammonium sulfate solution obtained in the caprolactam formation step was:

| | |
|---|---|
| Ammonium sulfate | ca. 44 wt. % |
| Water | ca. 56 wt. % |
| Free $H_2SO_4$ | <0.1 wt. % |
| COD | 1200 ppm |
| Ammonium nitrate | <0.01 wt. % |

COD (chemical oxygen demand) content, which is a measure for the concentration organic impurities, refers to values as determined according to ASTM D 1252-95 (dichromate method).

The volume:volume ratio of aqueous ammonium sulfate solution obtained in the cyclohexanone oxime formation step to the aqueous ammonium sulfate solution obtained in the caprolactam formation step was approximately 5:3.

By addition of aqueous ammonia (about 25 wt. %) the pH value of both ammonium sulfate solutions were increased to about 5 (as determined at a temperature of 25° C.).

The resulting solutions were fed to two lines of each four crystallization sections, in a system depicted in FIG. 3.

To crystallization sections (1), (2), (1a), (2a) and (3a) the pH adjusted aqueous ammonium sulfate solution obtained in the cyclohexanone oxime formation step was fed via line (5e). To crystallization sections (3), (4) and (4a) the pH adjusted aqueous ammonium sulfate solution obtained in the caprolactam formation step was fed via line (5f). To each crystallization section roughly a similar amount of ammonium sulfate solution was fed.

The crystallizers in the crystallization sections (1) and (1a) were operated at a temperature of about 115° C. The crystallizers in the crystallization sections (2) and (2a) were operated at a temperature of about 90° C. The crystallizers in the crystallization sections (3) and (3a) were operated at a temperature of about 70° C. And those in the sections (4) and (4a) were operated at a temperature of about 50° C. All crystallizers were of the Oslo crystallizer type.

The amount of fresh steam that were fed via lines (6) and (6a) to the crystallization sections (1) and (1a) was in each case about 10 ton/hr.

By purging aqueous ammonium sulfate solution, COD levels in the crystallization sections (4), (3a) and (4a) were kept at levels of approximately 40, 30 and 40 gram per kg clear solution, respectively. By purging aqueous ammonium sulfate solution, the ammonium nitrate levels in clear solution in the crystallization sections (1), (2), (1a), (2a) and (3a) were kept at levels of approximately 35 wt. %. From each crystallization section, ammonium sulfate solution containing ammonium sulfate crystals was discharged and fed to a centrifuge in which the crystals were separated from mother liquor and were washed with some water. Then the obtained washed crystals were dried.

The colour of the resulting ammonium sulfate crystals was white and no black coloured particles were observed between the salt crystals.

The production capacity of ammonium sulfate crystals of each crystallization section was about 60 kta.

This example shows that by feeding an aqueous ammonium sulfate solution obtained in the cyclohexanone oxime formation step to the crystallization sections that are operated at higher temperatures and feeding an aqueous ammonium sulfate solution obtained in the caprolactam formation step it is possible to produce ammonium sulfate crystals that are not polluted with black coloured particles.

The combined amount of fresh steam that was fed via lines (6) and (6a) to the crystallization sections (1) and (1a) was about 20 ton/hr, In case both aqueous ammonium sulfate solutions would have been fed to 8 crystallization sections without heat integration the total consumption of fresh steam would have been for each section about 10 ton/hr. So, this example further shows that steam (energy) consumption may be significantly reduced; in theory by 75%.

COMPARATIVE EXAMPLE 1

In a commercial caprolactam plant cyclohexanone oxime was produced according to the Raschig route from cyclohexanone produced via hydrogenation of phenol. The cyclohexanone oxime was converted into caprolactam in a multistage Beckmann rearrangement process with oleum. The obtained caprolactam was recovered after neutralization with aqueous ammonia. In each of the cyclohexanone oxime formation step and in the caprolactam formation step aqueous ammonia was used for neutralization and as a result an aqueous ammonium sulfate solution was obtained as by-product.

The volume:volume ratio of the amount of aqueous ammonium sulfate solution obtained in the cyclohexanone oxime formation step to the amount of aqueous ammonium sulfate solution obtained in the caprolactam formation step was approximately 5:3. These two aqueous ammonium sulfate solutions were blended.

The composition of the combined aqueous ammonium sulfate solutions was:

| | |
|---|---|
| Ammonium sulfate | ca. 43.7 wt. % |
| Water | ca. 55 wt. % |
| Free $H_2SO_4$ | <0.1 wt. % |
| COD | ca. 525 ppm |
| Ammonium nitrate | ca. 1.3 wt. % |

By addition of aqueous ammonia (about 25 wt. %) the pH value of combined ammonium sulfate solutions was increased to about 5 (as determined at a temperature of 25° C.).

The obtained pH adjusted aqueous ammonium sulfate solution was fed to all four crystallization sections of an experimental set-up as described in FIG. 1. To each crystallization section roughly a similar amount of ammonium sulfate solution was fed.

The temperatures of the crystallizers in the crystallization sections (1), (2), (3) and (4) were about 115° C., 90° C., 70° C. and 50° C., respectively.

In order to obtain the same overall ammonium sulfate crystal yield as Example 1 the ratios of purge flow over feed for each crystallizer were taken equal to those in Example 1. Specifically, the ratio of purge flow over feed of crystallization section (1) was taken equal to the average of the ratios of purge flow over feed of crystallization sections (1) and (1a) in Example 1; the ratio of purge flow over feed of crystallization section (2) was taken equal to the average of the ratios of purge flow over feed of crystallization sections (2) and (2a) in Example 1; the ratio of purge flow over feed of crystallization section (3) was taken equal to the average of the ratios of purge flow over feed of crystallization sections (3) and (3a) in Example 1; and the ratio of purge flow over feed of crystallization section (4) was taken equal to the average of the ratios of purge flow over feed of crystallization sections (4) and (4a) in Example 1.

From all crystallizers, the flows containing ammonium sulfate crystals were discharged and via centrifugation the crystals were separated from mother liquor and were washed with water. Then the obtained washed crystals were dried.

The colour of the resulting ammonium sulfate crystals obtained from crystallization sections (1) and (2) was brownish and black coloured particles could be observed between the salt crystals. In the ammonium sulfate crystals obtained from crystallization sections (3) and (4) no black coloured particles were observed.

This example shows that by feeding a blend of the aqueous ammonium sulfate solution obtained in the cyclohexanone oxime formation step and the aqueous ammonium sulfate solution obtained in the caprolactam formation step it is possible to produce ammonium sulfate crystals with the same overall ammonium sulfate crystal yield per tonne of produced ammonium sulfate crystals due to operating the crystallizers with the same purge to feed rates as Example 1. It is clear that after implementing this heat integration the same low overall consumption of heating steam per tonne of produced ammonium sulfate crystals can be obtained as Example 1.

However, due to the poor quality of the ammonium sulfate crystals produced in the crystallization sections (1) and (2) the average quality of all ammonium sulfate crystals produced in Comparative Example 1 is much worse than the average quality of all ammonium sulfate crystals produced in Example 1.

COMPARATIVE EXAMPLE 2

In this Comparative Example 2 the same blend of two aqueous ammonium sulfate solutions was used as in Comparative Example 1. By addition of aqueous ammonia (about 25 wt. %) the pH value of combined ammonium sulfate solutions was increased to about 5 (as determined at a temperature of 25° C.).

The obtained pH adjusted aqueous ammonium sulfate solution was fed to the crystallization sections (3) and (4) of an experimental set-up as described in FIG. 1. The crystallization sections (1) and (2) of the experimental set-up as described in FIG. 1 were not in operation. Fresh steam was fed to the crystallization section (3) via line (8). The temperatures of the crystallizers in the sections (3) and (4) were taken equal to those in Comparative Example 1: about 70° C. and 50° C., respectively.

The ratio of purge flow over feed of crystallization section (3) was taken equal to the ratio of purge flow over feed of crystallization section (3) in Comparative Example 1; and the ratio of purge flow over feed of crystallization section (4) was taken equal to the ratio of purge flow over feed of crystallization section (4) in Comparative Example 1.

From all crystallizers ammonium sulfate solution containing ammonium sulfate crystals was discharged and via centrifugation the crystals were separated from mother liquor and were washed with water. Then the obtained washed crystals were dried.

The resulting ammonium sulfate crystals obtained from crystallization sections (3) and (4) were white coloured and no black coloured particles were observed.

This example shows that by feeding a blend of the aqueous ammonium sulfate solution obtained in the cyclohexanone oxime formation step and the aqueous ammonium sulfate solution obtained in the caprolactam formation step it is possible to produce good quality ammonium sulfate crystals (white coloured and without black particles).

However, operating the evaporative crystallizers heat integrated in a series of just two instead of four results in an overall consumption of heating steam per tonne of produced ammonium sulfate crystals that is almost twice as high as the overall consumption of heating steam per tonne of produced ammonium sulfate crystals produced in Example 1.

COMPARATIVE EXAMPLE 3

In a commercial caprolactam plant caprolactam is produced from cyclohexanone oxime via a 3-stage Beckmann rearrangement process in oleum. The obtained caprolactam was recovered after neutralization of the reaction mixture with aqueous ammonia. The resulting aqueous ammonium containing sulfate solution was extracted with benzene to recover caprolactam. After stripping, the resulting aqueous ammonium sulfate containing solution was sent to the crystallization section. Here the pH value of the stripped aqueous ammonium containing sulfate solution which had a temperature of about 60° C. was adjusted by adding aqueous ammonia to a value of about 5 (as determined at a temperature of 25° C.). The resulting solution was fed to an Oslo type crystallizer that was operated at a temperature of about 115° C. The annual capacity of this Oslo crystallizer was about 75 kton ammonium sulfate crystals. By purging ammonium sulfate solution, the COD level in the crystallizer was kept at a level of approximately 15 gram per kg clear solution. Ammonium sulfate solution containing ammonium sulfate crystals was discharged from this crystallizer and fed to a centrifuge in which the crystals were separated from the mother liquor and washed with water. Then the obtained washed crystals were dried.

The colour of the resulting ammonium sulfate crystals was brownish, and black coloured particles that were irregularly shaped and of sizes up to a few millimeters could be observed between the salt crystals.

Four of these black coloured particles were hand-picked and analysed. The results of these analyses are shown in the next Table:

| Component | Particle 1 | Particle 2 | Particle 3 | Particle 4 |
|---|---|---|---|---|
| Water | 12.3 wt. % | 30.4 wt. % | 1.4 wt. % | 5.8 wt. % |
| Ammonia | 14.5 wt. % | 6.0 wt. % | 9.7 wt. % | 11.0 wt. % |
| Sulfate | 35.0 wt. % | 8.6 wt. % | 17.6 wt. % | 21.2 wt. % |
| Caprolactam | 0.16 wt. % | 0.14 wt. % | 0.16 wt. % | 0.5 wt. % |
| ε-aminocaproic acid | 0.28 wt. % | 0.22 wt. % | 0.43 wt. % | 0.43 wt. % |
| Disulfonated octahydrophenazine | 9.9 wt. % | 15.4 wt. % | 19.8 wt. % | 20.2 wt. % |
| Others | Balance | Balance | Balance | Balance |
| Non-aqueous soluble residue | 3.2 wt. % | 4.4 wt. % | 6.9 wt. % | 7.6 wt. % |

This Comparative Example 3 shows that undesired visible solid impurities are present when a feed of ammonium sulphate formed as by-product in the Beckmann rearrangement of cyclohexanone oxime to form caprolactam, when it is crystallized at a temperature of 115° C. Further, that these undesired visible solid impurities have a high organic content.

The invention claimed is:

1. A continuous process for producing ammonium sulfate crystals, wherein said process comprises:
   (a) feeding to a first group of crystallization sections, which crystallization sections are heat integrated in series, a first aqueous ammonium sulfate solution that contains one or more impurities;
   (b) feeding to a second group of crystallization sections, which crystallization sections are heat integrated in series, a second aqueous ammonium sulfate solution that contains one or more impurities;
   (c) crystallizing ammonium sulfate crystals in each crystallization section respectively from each of said solutions of ammonium sulfate that contain one or more impurities;
   (d) purging a fraction of the ammonium sulfate solution that contains one or more impurities from each of said crystallization sections; and
   (e) discharging ammonium sulfate crystals from each crystallization section,
   characterized in that:
   (i) both the first group of crystallization sections and the second group of crystallization sections are together heat integrated in one series of crystallization sections; wherein the first group of crystallization sections operates at higher temperature than the second group of crystallization sections; and
   (ii) the composition of the first aqueous ammonium sulfate solution that contains one or more impurities is different to the composition of the second aqueous ammonium sulfate solution that contains one or more impurities; and (iii) the first aqueous ammonium sulfate solution that contains one or more impurities and the second aqueous ammonium sulfate solution that contains one or more impurities are each independently produced as by-products during the production of cyclohexanone oxime, caprolactam, or acrylonitrile.

2. A process according to claim 1, wherein the crystallization sections are heat integrated by means of steam.

3. A process according to claim 2, wherein the temperature of steam entering the first crystallization section in the series of crystallization sections is from 80° C. to 160° C.

4. A process according to claim 3, wherein the temperature of steam exiting the last crystallization section in the series of crystallization sections is from 45° C. to 75° C.

5. A process according to claim 1, wherein the first aqueous ammonium sulfate solution that contains one or more impurities is produced as a by-product during the production of cyclohexanone oxime by oximation of cyclohexanone with aqueous hydroxylammonium sulfate.

6. A process according to claim 1, wherein the second aqueous ammonium sulfate solution that contains one or more impurities is produced as a by-product during the production of caprolactam obtained by Beckmann rearrangement of cyclohexanone oxime in either oleum, sulfuric acid, or $SO_3$.

7. A process according to claim 1, wherein the series of crystallization sections comprises from 2 to 5 crystallization sections.

8. A process according to claim 1, wherein each crystallization section in the series of crystallization sections has substantially equal production capacity of ammonium sulfate crystals.

9. A process according to claim 1, wherein a fraction of aqueous ammonium sulfate solution that also contains one or more impurities is purged from at least one crystallization section in a group to at least one other crystallization section in the same group.

10. A process according to claim 9, wherein the crystallization sections are heat integrated by means of steam, and a fraction of aqueous ammonium sulfate solution that also contains one or more impurities is purged from each crystallization section in a group to the next crystallization section, as defined by descending temperature of steam supply, in the same group, with the exception that the purge from the final crystallization section in the group is discharged from the group.

* * * * *